US009499787B2

(12) United States Patent
Park et al.

(10) Patent No.: US 9,499,787 B2
(45) Date of Patent: Nov. 22, 2016

(54) METHOD FOR DIFFERENTIATING STEM CELLS INTO NEURONS

(71) Applicant: Dongguk University Industry-Academic Cooperation Foundation, Seoul (KR)

(72) Inventors: Jung Keug Park, Seoul (KR); Hee Hoon Yoon, Gyeonggi-do (KR); Soo Yeon Kim, Gyeonggi-do (KR); Young Kwon Seo, Seoul (KR)

(73) Assignee: Dongguk University Industry—Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/377,160

(22) PCT Filed: Feb. 5, 2013

(86) PCT No.: PCT/KR2013/000928
§ 371 (c)(1),
(2) Date: Aug. 6, 2014

(87) PCT Pub. No.: WO2013/119026
PCT Pub. Date: Aug. 15, 2013

(65) Prior Publication Data

US 2015/0004701 A1 Jan. 1, 2015

(30) Foreign Application Priority Data

Feb. 6, 2012 (KR) ........................ 10-2012-0011717

(51) Int. Cl.
*C12N 5/079* (2010.01)

(52) U.S. Cl.
CPC ......... *C12N 5/0618* (2013.01); *C12N 2500/44* (2013.01); *C12N 2501/33* (2013.01); *C12N 2501/39* (2013.01); *C12N 2501/999* (2013.01); *C12N 2506/1346* (2013.01); *C12N 2506/1384* (2013.01)

(58) Field of Classification Search
None
See application file for complete search history.

(56) References Cited

U.S. PATENT DOCUMENTS

| | | | |
|---|---|---|---|
| 5,232,848 A | 8/1993 | Wolfe et al. | |
| 8,058,243 B2 * | 11/2011 | Tyers et al. | 514/19.3 |
| 2010/0173409 A1 | 7/2010 | Gardner et al. | |

FOREIGN PATENT DOCUMENTS

| | | |
|---|---|---|
| KR | 10-2004-0088169 | 10/2004 |
| KR | 10-2011-0066443 | 6/2011 |

OTHER PUBLICATIONS

Qian, Lichuan; Saltzman, W. Mark; "Improving the expansion and neuronal differentiation of mesenchymal stem cells through culture surface modification" Biomaterials, 25, 1331-1337, 2004.*
Dezawa, Mari; et al; "Specific induction of neuronal cells from bone marrow stromal cells and application for autologous transplantation" The Journal of Clinical Investigations, 113, 1701-1710, 2004.*
Long, Xiaoxiao; et al; "Neural Cell Differentiation In Vitro from Adult Human Bone Marrow Mesenchymal Stem Cells" Stem Cells and Development, 65-69, 2005.*
International Preliminary Report on Patentability and Written Opinion for PCT/KR2013/000928, issued Aug. 12, 2014, 10 pages (English translation included).
International Search Report for PCT/KR2013/000928, mailed May 29, 2013, 6 pages (English translation included).
Kunt et al., "Alpha-lipoic acid reduces expression of vascular cell adhesion molecule-1 and endothelial adhesion of human monocytes after stimulation with advanced glycation end products," Clin Sci (Lond) (1999) 96(1):75-82.

* cited by examiner

*Primary Examiner* — Renee Claytor
*Assistant Examiner* — David Berke-Schlessel
(74) *Attorney, Agent, or Firm* — Morrison & Foerster LLP

(57) ABSTRACT

The present invention relates to a method for differentiating stem cells into neurons, and is characterized in that stem cells are treated with a culture additive comprising lipoic acid, albumin, hydrocortisone, and insulin after culturing for differentiation into neurons. Since the neurons produced according to the method for producing neurons of the present invention express nestin, neuroD1, neuron-specific enolase (NSE), neurofilament (NF), tau, microtubule-associated protein 2 (MAP2), and doublecortin (DCX), just as normal mature neurons do, the neurons of the present invention can be effectively used in various therapeutic agents for neurons and as cell origins for an in vitro study system.

10 Claims, 5 Drawing Sheets

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Forward primer of MAP2

<400> SEQUENCE: 1

ctcaacagtt ctatctcttc ttca                                   24


<210> SEQ ID NO 2
<211> LENGTH: 24
```

-continued

<212> TYPE: DNA
<213> ORGANISM: Artificial Sequence
<220> FEATURE:
<223> OTHER INFORMATION: Reverse primer of MAP2

<400> SEQUENCE: 2
tcttcttgtt taaaatccta acct 24

<210> SEQ ID NO 3
<211> LENGTH: 21
<212> TYPE: DNA
<213> ORGANISM: Artificial Sequence
<220> FEATURE:
<223> OTHER INFORMATION: Forward primer of DCX

<400> SEQUENCE: 3
ggaaggggaa agctatgtct g 21

<210> SEQ ID NO 4
<211> LENGTH: 20
<212> TYPE: DNA
<213> ORGANISM: Artificial Sequence
<220> FEATURE:
<223> OTHER INFORMATION: Reverse primer of DCX

<400> SEQUENCE: 4
ttgctgctag ccaaggactg 20

<210> SEQ ID NO 5
<211> LENGTH: 22
<212> TYPE: DNA
<213> ORGANISM: Artificial Sequence
<220> FEATURE:
<223> OTHER INFORMATION: Forward primer of Tau

<400> SEQUENCE: 5
gtaaaagcaa agacgggact gg 22

<210> SEQ ID NO 6
<211> LENGTH: 22
<212> TYPE: DNA
<213> ORGANISM: Artificial Sequence
<220> FEATURE:
<223> OTHER INFORMATION: Reverse primer of Tau

<400> SEQUENCE: 6
atgatggatg ttgcctaatg ag 22

<210> SEQ ID NO 7
<211> LENGTH: 25
<212> TYPE: DNA
<213> ORGANISM: Artificial Sequence
<220> FEATURE:
<223> OTHER INFORMATION: Forward primer of NeuroD1

<400> SEQUENCE: 7
ccgacagagc ccagatgtag ttctt 25

<210> SEQ ID NO 8
<211> LENGTH: 25
<212> TYPE: DNA
<213> ORGANISM: Artificial Sequence
<220> FEATURE:
<223> OTHER INFORMATION: Reverse primer of NeuroD1

<400> SEQUENCE: 8

-continued

```
gccccagggt tatgagacta tcact                                       25


<210> SEQ ID NO 9
<211> LENGTH: 19
<212> TYPE: DNA
<213> ORGANISM: Artificial Sequence
<220> FEATURE:
<223> OTHER INFORMATION: Forward primer of NSE

<400> SEQUENCE: 9

ggcgggcagt ggaagaaaa                                              19


<210> SEQ ID NO 10
<211> LENGTH: 20
<212> TYPE: DNA
<213> ORGANISM: Artificial Sequence
<220> FEATURE:
<223> OTHER INFORMATION: Reverse primer of NSE

<400> SEQUENCE: 10

aagtggaaag tgcggaaccc                                             20


<210> SEQ ID NO 11
<211> LENGTH: 20
<212> TYPE: DNA
<213> ORGANISM: Artificial Sequence
<220> FEATURE:
<223> OTHER INFORMATION: Forward primer of Nestin

<400> SEQUENCE: 11

ctctgacctg tcagaagaat                                             20


<210> SEQ ID NO 12
<211> LENGTH: 20
<212> TYPE: DNA
<213> ORGANISM: Artificial Sequence
<220> FEATURE:
<223> OTHER INFORMATION: Reverse primer of Nestin

<400> SEQUENCE: 12

gacgctgaca cttacagaat                                             20


<210> SEQ ID NO 13
<211> LENGTH: 20
<212> TYPE: DNA
<213> ORGANISM: Artificial Sequence
<220> FEATURE:
<223> OTHER INFORMATION: Forward primer of NF-L

<400> SEQUENCE: 13

gccaagaaca tgcagaacgc                                             20


<210> SEQ ID NO 14
<211> LENGTH: 20
<212> TYPE: DNA
<213> ORGANISM: Artificial Sequence
<220> FEATURE:
<223> OTHER INFORMATION: Reverse primer of NF-L

<400> SEQUENCE: 14

cagctttaat gcggaacgcc                                             20


<210> SEQ ID NO 15
<211> LENGTH: 20
<212> TYPE: DNA
<213> ORGANISM: Artificial Sequence
```

-continued

```
<220> FEATURE:
<223> OTHER INFORMATION: Forward primer of GAPDH

<400> SEQUENCE: 15

accacagtcc atgccatcac                                                20


<210> SEQ ID NO 16
<211> LENGTH: 20
<212> TYPE: DNA
<213> ORGANISM: Artificial Sequence
<220> FEATURE:
<223> OTHER INFORMATION: Reverse primer of GAPDH

<400> SEQUENCE: 16

ttcaccaccc tgttgctgta                                                20
```

METHOD FOR DIFFERENTIATING STEM CELLS INTO NEURONS

CROSS-REFERENCE TO RELATED APPLICATIONS

This application is a U.S. National Phase Application of international application PCT/KR2013/000928, filed Feb. 5, 2013, published as WO2013/119026 on Aug. 15, 2013, which claims benefit of priority from Korean Patent Application No.: 10-2012-0011717, filed Feb. 6, 2012. The contents of the above-referenced applications are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739882000100SeqList.txt, date recorded: Aug. 6, 2014, size: 3,818 KB).

TECHNICAL FIELD

The present invention relates to a method for differentiating stem cells into neural cells.

BACKGROUND ART

Stroke, Alzheimer's disease, Parkinson's disease, demyelinating disease, spinal cord injury, etc. are diseases caused by nerve dysfunction due to nerve cell damage. Methods for treating nerve cells damaged by these diseases typically include drug therapy and surgical operation, but these treatments may also damage normal cells, which is problematic.

Accordingly, cell therapy products used to replace cells lost or damaged by disease with normal cells have recently been proposed. Stem cells have attracted much attention as one of the cell therapy products.

Studies suggesting that mesenchymal stem cells (MSCs) can differentiate into neural cells have been published since the early 2000's and have extended to in vivo studies as well as in vitro studies. In order to examine the signal transduction mechanisms and changes in gene expression during the differentiation of mesenchymal stem cells into neural cells, in vivo transplantation studies are ultimately required, but there are also disadvantages such as high costs and time and many obstacles (various signal transductions), and thus it is not easy to conduct such studies. Moreover, as the cell therapy products for regenerative medicine in the future, it is not clear whether undifferentiated MSCs or neural-committed MSCs are effective for in vivo transplantation. Accordingly, in order to solve these problems, it is necessary to establish an appropriate technology that can differentiate mesenchymal stem cells into neural cells in vitro. There are generally two neural cell differentiation methods; one is chemical differentiation and the other is growth factor or cytokine differentiation. Chemical differentiation uses antioxidants, such as β-mercaptoethanol (BME), butylated hydroxyanisole (BHA), butylated hydroxyl toluene (BHT), retinoic acid (RA), etc., and induces the expression of neuronal markers, such as neuron-specific enolase (NSE), neurofilament (NF), neuronal nuclei (NeuN), etc., together with more severe morphological changes than the growth factor or cytokine differentiation. However, it is known that more than 50% cells undergo apoptosis along with these changes within 24 hours from the induction, and it is also known that chemicals induce cellular stress, which causes physical contraction of cells, like neurons, resulting in no expression of neuronal markers. This phenomenon occurs similarly when harmful substances are treated with other types of primary cells or transformed cells, and when summarizing these results, the treatment with antioxidants does not induce transdifferentiation into neural cells but simply causes environmental stress.

The growth factor or cytokine differentiation is a method for differentiating stem cells into neural cells by treatment with epidermal growth factor (EGF), fibroblast growth factor (FGF), nerve growth factor (NGF), brain-derived neurotrophic factor (BDNF), etc. and does not cause environmental stress or cell apoptosis. However, it takes more than 4 weeks to induce differentiation, which significantly increases the cost of differentiation. Nevertheless, the rate of differentiation into neurons is significantly low, and the expression of neuronal markers is different from that of mature neurons, which are also problematic.

Meanwhile, lipoic acid is a fatty acid containing sulfur atoms, represented by the following Formula 1, and is known as an alpha-lipoic acid. Moreover, it participates in energy metabolism that converts glucose into energy and is present in all eukaryotic cells. Furthermore, it is reported that lipoic acid essentially has antioxidation activity and thus also has anti-apoptotic activity. Accordingly, it is much used in serum-free culture of human cells, but is known to cause cell apoptosis at a concentration of 2 mM or higher and thus is used at concentrations as low as 25 to 100 μM.

[Formula 1]

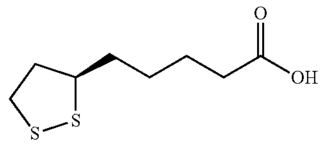

Accordingly, the present inventors have developed a new chemical neuronal differentiation method, which uses lipoic acid and albumin that reduces the toxicity of lipoic acid at high concentrations of lipoic acid and allows lipoic acid to be slowly released under culture conditions, and revealed that forskolin exhibits an additional synergistic effect on the neuronal differentiation, thereby completing the present invention.

DISCLOSURE OF THE INVENTION

Technical Problem

Accordingly, an object of the present invention is to provide a method for differentiating stem cells into neural cells and a composition for inducing neural cell differentiation.

Technical Solution

The present invention provides a method for differentiating stem cells into neural cells, the method comprising the steps of:

(a) culturing stem cells; and (b) differentiating the stem cells cultured in (a) into neural cells by treatment with a culture additive containing lipoic acid, albumin, hydrocortisone, and insulin.

Moreover, the present invention provides a method for differentiating stem cells into neural cells, in which the culture additive in step (b) further comprises forskolin or a nerve growth factor.

Furthermore, the present invention provides a composition for inducing neural cell differentiation, comprising lipoic acid, albumin, hydrocortisone, and insulin.

Advantageous Effects

The neural cells produced by the method according to the present invention express genes and proteins for nestin, NeuroD1, neuron-specific enolase (NSE), neurofilament (NF), tau, microtubule-associated protein 2 (MAP2), doublecortin (DCX), etc., which are similar to normal mature neurons, and thus can be used as various neural cell therapy products and cell sources for in vitro analysis systems.

MODES OF CARRYING OUT THE INVENTION

Figure 1:
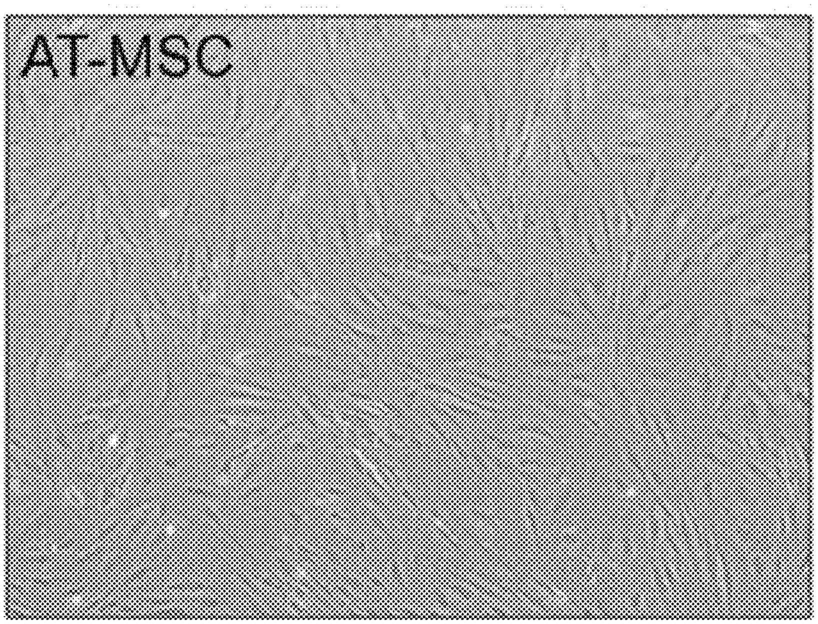
FIG. 1 shows a microscope image of mesenchymal stem cells isolated and cultured from adipose tissue (AT).

The present invention provides a method for differentiating stem cells into neural cells, the method comprising the steps of:

(a) culturing stem cells; and (b) differentiating the stem cells cultured in (a) into neural cells by treatment with a culture additive containing lipoic acid, albumin, hydrocortisone, and insulin.

The types of stem cells that can differentiate into neural cells according to the present invention are not limited, and any cells that have the properties of stem cells such as non-differentiation, indefinite proliferation, and the ability to differentiate into specific cells can be used. The stem cells include embryonic stem cells, adult stem cells, induced pluripotent stem cells, embryonic germ cells, embryonal carcinoma cells, neural stem cells, and mesenchymal stem cells, preferably mesenchymal stem cells.

The stem cells may be isolated from human bone marrow, umbilical cord blood, or adipose tissue. For example, when mononuclear cells are isolated from bone marrow and cultured for 1 to 2 weeks, haematopoietic stem cells, which can easily differentiate, differentiate to form blood cells, and thus only mesenchymal stem cells can be easily obtained by isolating the remaining stem cells, immortalized cells. Moreover, even when the mononuclear cells including mesenchymal stem cells are cultured by the method according to the present invention, instead of isolating mesenchymal stem cells from mononuclear cells isolated from bone marrow, the effect of mass production of neural cells can also be obtained. In preferred embodiments of the present invention, mesenchymal stem cells obtained from adipose tissue were cultured and used.

As used herein, the term "neural cells" refers to neurons and/or glia of central nervous system or peripheral nervous system, such as astrocytes, oligodendrocytes and/or Schwann's cells, and the differentiation into neural cells was determined using morphological characteristics and molecular biological characteristics in the present invention.

For the culture according to the present invention, Dulbecco's modified Eagle's medium (DMEM/F-12, F-12, McCoy's 5A, RPMI1640), Williams' medium E, or Iscoves' modified Dulbecco's medium (IMDM) can be used as a basic medium, and serum-free DMEM/F-12 is preferred in the present invention.

The medium may be supplemented with fetal calf serum (FCS) or fetal bovine serum (FBS), as well as antibiotics, growth factors, amino acids, inhibitors or the like, and the medium may preferably contain lipoic acid, albumin, hydrocortisone, and insulin.

The lipoic acid is known as an alpha-lipoic acid and participates in energy metabolism that converts glucose into energy and thus is present in all eukaryotic cells. The lipoic acid may preferably be contained in the culture medium at a concentration of 3 mM to 15 mM, more preferably at a concentration of 4 mM to 8 mM.

The albumin may include serum albumin, ovalbumin, etc., but serum albumin is preferred. The origin of albumin is not particularly limited, and the albumin may include those derived from humans or other warm-blooded animals (for example, cows, monkeys, pigs, pigs, horses, sheep, goats, dogs, cats, rabbits, mice, rats, hamsters, guinea pigs, chickens, quails, etc.), preferably human albumin, more preferably human serum albumin (HAS) for the use as a carrier of drugs or pharmaceutical compounds. Sugar chain-containing albumin can be produced and used by those skilled in the art based on the sequence information of albumin described in the specification and other albumins known in the art. The albumin may be contained in an amount of 0.1 wt % to 5 wt % with respect to the total weight of the culture medium, preferably in an amount of 1 wt %.

The hydrocortisone is an organic compound with two isomers, 4-tert-butyl-4-hydroxyanisole and 3-tert-butyl-4-hydroxyanisole, and has antioxidant properties. The hydrocortisone is known to inhibit intracellular signaling pathways, such as nuclear factor KB activity, regulated by active oxygen species. The hydrocortisone may be contained in the culture medium at a concentration of 0.01 uM to 10 uM, preferably at a concentration of 1 uM.

The insulin is a hormone secreted from the β-cells of the islets of Langerhans and maintains normal blood glucose levels. The insulin may be contained in the culture additive of the present invention at a concentration of 1 mg/ml to 50 mg/ml, preferably 10 mg/ml.

Moreover, in the method for differentiating stem cells into neural cells according to the present invention, the culture additive may further include forskolin or a nerve growth factor for neural cell differentiation.

The forskolin (7 beta-acetoxy-8,13-epoxy-1 alpha, 6 beta, 9 alpha-trihydroxy-labd-14-ene-11-one) activates adenyl cyclase and increases cyclic AMP (cAMP) to stimulate the cell receptor. Cyclic AMP (cAMP) is an important signal carrier necessary for the proper biological response of cells to hormones and plays an important role in the mechanism involved in the activation of protein transcription necessary for cell survival and differentiation. In the present invention, the method for differentiating stem cells into neural cells using the culture additive containing lipoic acid, albumin, hydrocortisone, and insulin may further promote the neural cell differentiation by further treating with forskolin. The forskolin may be contained in the culture medium at a concentration of 0.1 uM to 10 uM, preferably at a concentration of 1 uM.

The nerve growth factor refers to a cytokine peptide that induces differentiation and growth of neural cells and tissue. The nerve growth factor may be at least one selected from the group consisting of brain-derived neurotrophic factor (BDNF), vascular endothelial growth factor (VEGF), hepatocyte growth factor (HGF), nerve growth factor (NGF), basic fibroblast growth factor (bFGF), glial cell line-derived neurotrophic factor (GDNF), and platelet-derived growth factor (PDGF), but not limited thereto. The never growth factor may be contained in the culture medium at a concentration of 5 ng/ml to 20 ng/ml, preferably at a concentration of 10 ng/ml.

Moreover, the present invention provides a composition for inducing neural cell differentiation, comprising lipoic acid, albumin, hydrocortisone, and insulin.

The composition is used to differentiate mesenchymal stem cells into neural cells in vitro. The neural cells proliferated in vitro using the composition can be transplanted into a lesion site and thus can be effectively used for cell therapy.

The composition is used to differentiate mesenchymal stem cells into neural cells in vivo. Specifically, after transplanting mesenchymal stem cells into a lesion site, the composition may be continuously injected into the transplantation site such that neural cells can be effectively generated in vivo. This method is to transplant mesenchymal stem cells into a lesion site that requires neural cells, prior to differentiation, and then induce differentiation into neural cells, and thus it is possible to promote nerve regeneration and functional recovery through treatment of intractable neurological diseases by transplantation of mesenchymal stem cells.

The neural cells produced by the method according to the present invention express genes and proteins for nestin, NeuroD1, neuron-specific enolase (NSE), neurofilament (NF), tau, microtubule-associated protein 2 (MAP2), doublecortin (DCX), etc., which are similar to normal mature neurons, and thus can be used as various neural cell therapy products and cell sources for in vitro analysis systems.

Mode for Invention

Hereinafter, preferred Examples will be provided for better understanding of the present invention. However, the following Examples are provided only to facilitate understanding of the present invention, and the present invention is not limited thereto.

Example 1

Culture of Mesenchymal Stem Cells From Adipose Tissue

Mesenchymal stem cells obtained from adipose tissue used in this Example were StemPro® Adipose-derived Stem Cells (Product No. R7788-110) purchased from Invitrogen. Frozen ampoules were thawed, and cells were washed with DMEM, centrifuged at 800 RPM for 5 minutes, and cultured in DMEM containing low glucose (1000 mg/L) and supplemented with 10% fetal bovine serum (FBS). The cultured cells were observed, and the results are shown in FIG. 1.

As shown in FIG. 1, the cultured cells resembled fibroblasts and were maintained up to 10 generations without a decrease in proliferation. Therefore, it can be seen that the cultured cells have the morphological characteristics of mesenchymal stem cells.

Example 2

Identification of Mesenchymal Stem Cells

In order to identify whether the cells cultured in Example 1 were mesenchymal stem cells, a fluorescence-activated cell sorter (FACS) analysis and an analysis of connective tissue cell differentiation capacity were performed as follows.

1. FACS Analysis

The FACS analysis with a fluorescence-activated cell sorter (BD Bioscience) showed that all of the cells were positive for markers of mesenchymal stem cells such as CD90, CD73, and CD105 and negative for markers of haematopoietic cells such as CD14, CD34, and CD45. Therefore, all of the cultured cells exhibited the expression characteristics of surface antigens of mesenchymal stem cells. The results are shown in FIG. 2.

Figure 2:
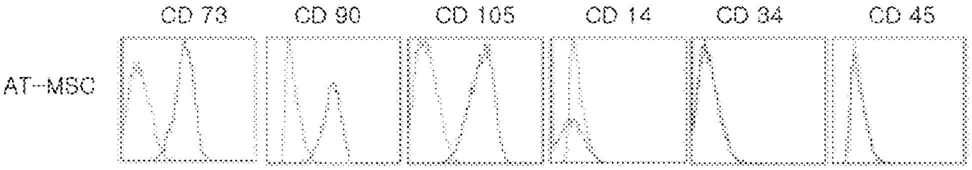
FIG. 2 shows the results of fluorescence-activated cell sorter (FACS) analysis on the expression of surface antigens such as CD73, CD90, CD105, CD14, CD34, and CD45 of mesenchymal stem cells.

As shown in FIG. 2, it can be seen that the activated cells expressing the surface antigens, which can be observed in mesenchymal stem cells, are uniformly distributed.

2. Connective Tissue Cell Differentiation Capacity

In order to differentiate the cells cultured in Example 1 into osteoblasts, the cells were cultured at high density and then cultured in DMEM containing high glucose (4000 mg/L) and supplemented with 100 nM dexamethasone, 0.05 mM ascorbic acid 2-phosphate, 10 mM beta-glycerophosphate (Sigma-Aldrich Co.), and 10% fetal bovine serum (FBS) for four weeks.

Moreover, in order to differentiate the cells cultured in Example 1 into chondrocytes, 2×105 cells were centrifuged to form pellets, which were cultured in DMEM containing high glucose (4000 mg/L) and supplemented with 1 mM sodium pyruvate, 0.1 mM ascorbic acid 2-phosphate, 10-7 M dexamethasone, 5 μg/ml insulin, 5 μg/ml transferrin, 0.5 ng/ml selenium (ITS; Sigma-Aldrich Co.), and 10 ng/ml transforming growth factor-β (TGF-β, R & D Systems Inc.) for four weeks.

Furthermore, in order to differentiate the cells cultured in Example 1 into adipocytes, the cells cultured at high density were cultured in DMEM containing high glucose and supplemented with 1 μM dexamethasone, 0.05 mM methylisobutylxanthine, 10 μg/ml insulin, 100 μM indomethacin (Sigma-Aldrich Co.), and 10% fetal bovine serum (FBS) for three days and cultured in DMEM supplemented with 10 μg/ml insulin and 10% fetal bovine serum (FBS) for one day, which were alternated for four weeks.

Figure 3:
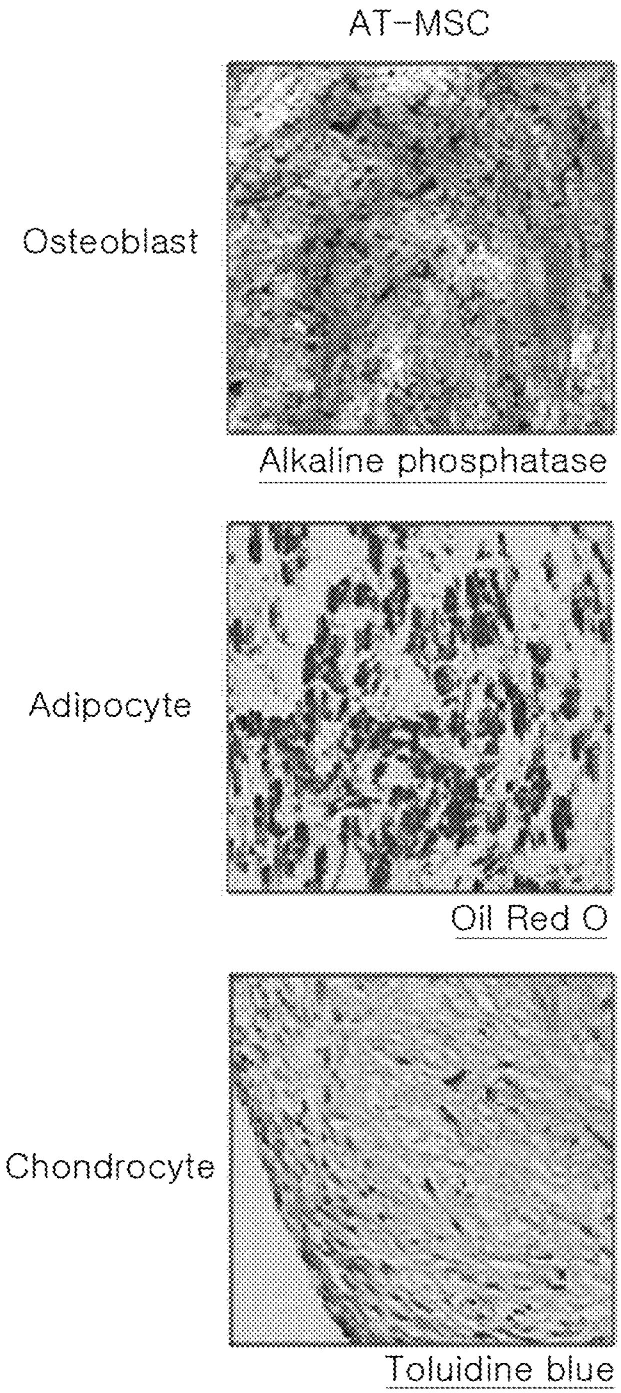
FIG. 3 shows the results of differentiation of mesenchymal stem cells into osteoblasts, chondrocytes, and adipocytes.

The cells differentiated into osteoblasts, chondrocytes, and adipocytes were identified by alkaline phosphatase staining, toluidine blue staining, and oil red O staining, respectively, and the results are shown in FIG. 3.

As shown in FIG. 3, it can be seen that the cultured cells have the morphological characteristics of osteoblasts, chondrocytes, and adipocytes, respectively.

Example 3

Differentiation Into Neural Cells

Mesenchymal stem cells were seeded in low glucose-Dulbecco's Modified Eagle's Medium (LG-DMEM) containing 10% fetal bovine serum (FBS) at a density of 5×103 cell/cm2. 24 hours after seeding, the medium was replaced with fresh DMEM/F-12 (1:1 mixed medium) supplemented with 1 uM hydrocortisone, 10 mg/ml insulin, 1% bovine serum albumin, and 0, 1, 2, 3, 4, 5 or 8 mM lipoic acid to induce differentiation into neural cells. Moreover, 1 uM forskolin was further added to promote differentiation into neural cells. The cellular morphology of neural cells was observed under a microscope, and the results are shown in FIGS. 4 and 5.

Figure 4:
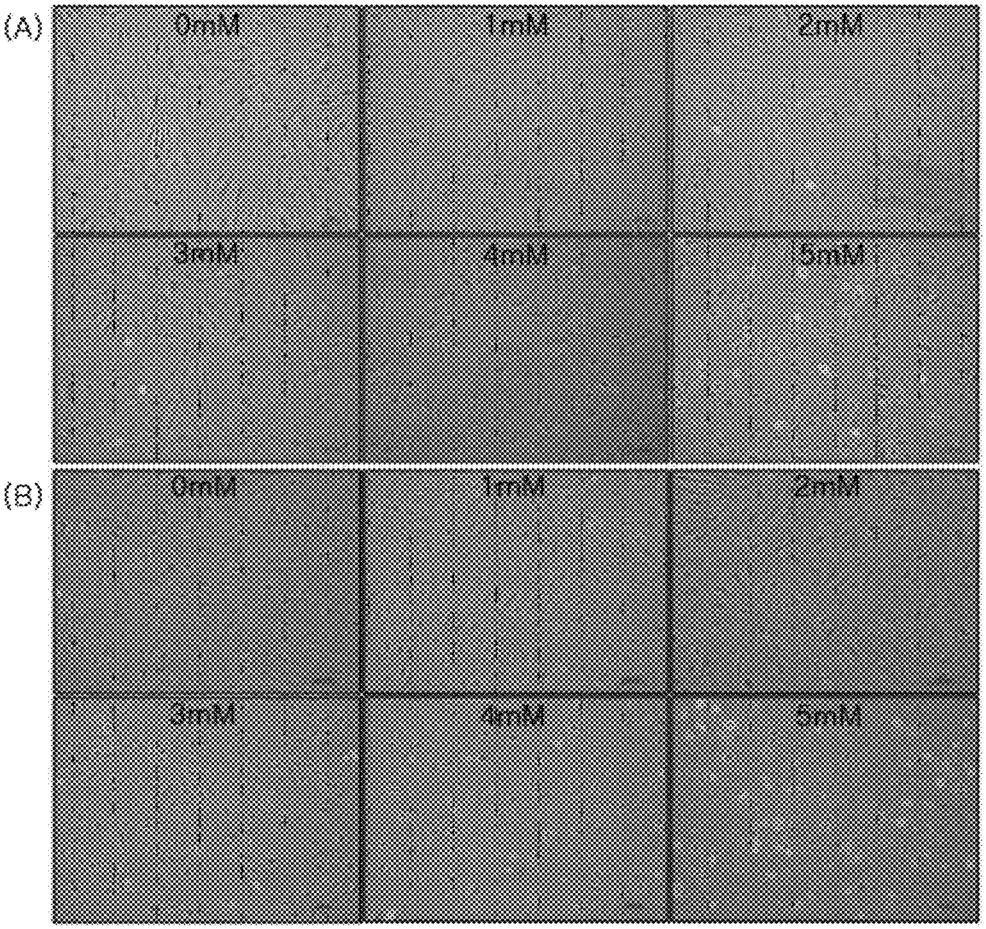
FIG. 4 shows microscope images of cellular morphology obtained after treating mesenchymal stem cells with a culture additive containing lipoic acid, albumin, hydrocortisone, and insulin according to a chemical neuronal differentiation method.

As shown in FIG. 4, it can be seen from the morphological changes of neural cells observed under a microscope that dendrites were well formed with lipoic acid at more than 2 mM at 5 days. However, there was no change with lipoic acid at 0 and 1 mM. This phenomenon can be confirmed by the fact that the cell viability was maintained by the sustained-release of 1% albumin and the dendrites were well formed, unlike the previous report that lipoic acid at more than 2 mM causes apoptosis. Moreover it was found that lipoic acid was well maintained up to 5 days, unlike the morphology of neural cells, which was observed upon treatment with butylated hydroxyanisole, was destroyed after 24 hours.

Figure 5:
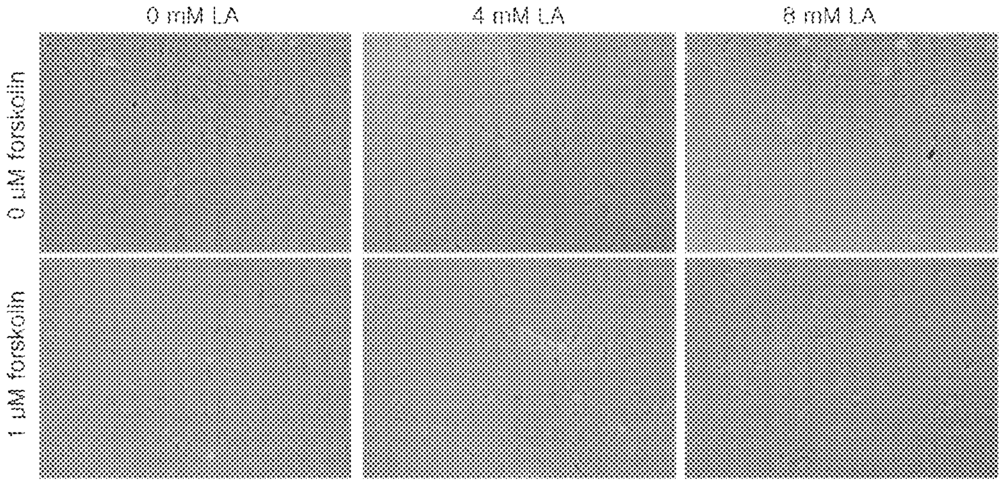
FIG. 5 shows microscope images of cellular morphology obtained after treating mesenchymal stem cells with a culture additive containing lipoic acid, albumin, hydrocortisone, and insulin and further treating with forskolin according to a chemical neuronal differentiation method. (국문명세시에시 노 변 확인 바랍니다)

Moreover, as shown in FIG. 5, it was found that the additional treatment with 1 ug forskolin increased the rate of differentiation into neural cells.

Experimental Example 1

Measurement of Cell Viability of Neural Cells

The cell viability was measured by MTT (3-(4,5-dimethylthiazol-2-yl)-2,5-diphenyltetrazolium bromide). Specifically, MTT solution (0.0333 g/ml DMEM) was added to the neural cells cultured in Example 3 for reaction at 37° C. for 90 minutes and then removed. Then, dimethyl sulfoxide (DMSO) was added and left to stand for 10 minutes, and the resulting solution was used to measure the absorbance at 570 nm using a spectrum analyzer. Mesenchymal stem cells were seeded in low glucose-Dulbecco's Modified Eagle's Medium (LG-DMEM) containing 10% fetal bovine serum (FBS) at a density of 5×103 cell/cm2. 24 hours after seeding, the medium was replaced with fresh DMEM/F-12 (1:1 mixed medium) supplemented with 1 ug hydrocortisone, 10 mg/ml insulin, 1% bovine serum albumin, and 0, 1, 2, 3, 4, 5 or 8 mM lipoic acid to induce differentiation into neural cells. Moreover, 1 ug forskolin or 10 mg/ml nerve growth factor (NGF) might be further added to enhance differentiation into neural cells. The cells treated with 200 mM butylated hydroxyanisole (BHA) were used as a control. The results are shown in FIG. 6.

Figure 6:
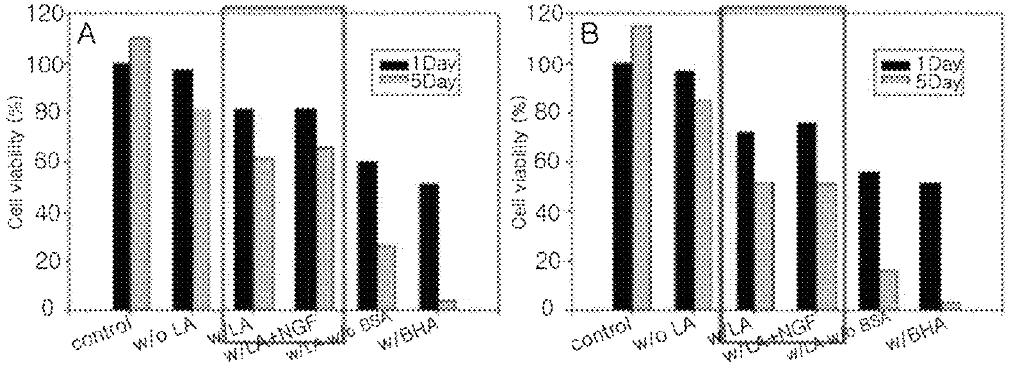
FIG. 6 shows the cell viability of mesenchymal stem cells treated with lipoic acid according to a chemical neuronal differentiation method.

As shown in FIG. 6, the cell viability at 5 days was too low in the conditions containing 4 and 8 mM lipoic acid and no 1% albumin and in the condition containing 200 ug butylated hydroxyanisole and thus these conditions could not be used for cell differentiation. However, it was found that the cell viability was as high as 61.4%, 65.5% (+nerve growth factor), and 51.4%, 50.9% (+nerve growth factor), respectively, even up to 5 days in the lipoic acid condition containing 1% albumin. In this regard, it is believed that the albumin enhances the cell viability as it acts as a carrier for lipoic acid and exhibits a sustained-release effect.

Experimental Example 2

Reverse Transcription-Polymerase Chain Reaction (RT-PCR) of Neural Cells

Figure 7:
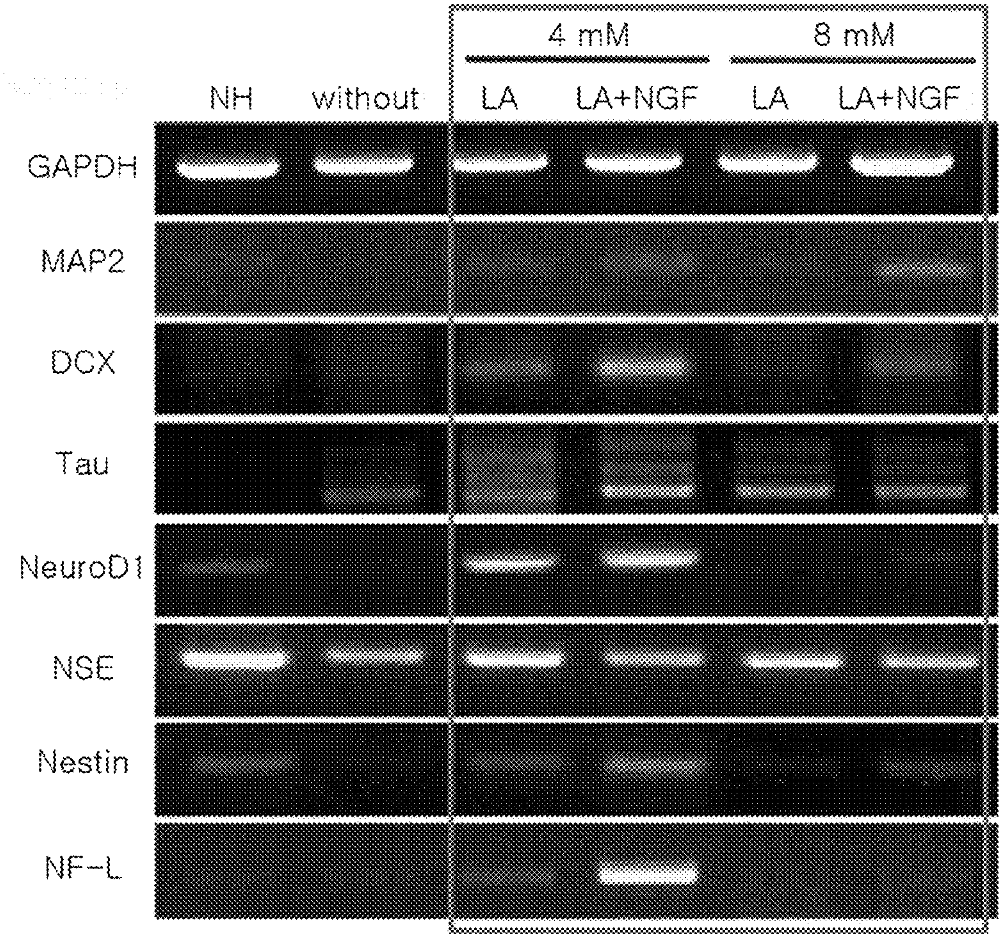
FIG. 7 shows the results of the expression of neuron-specific genes after treating mesenchymal stem cells with lipoic acid according to a chemical neuronal differentiation method, determined by reverse transcription polymerase chain reaction.

The total RNA was recovered and isolated using TRIzol® solution (Invitrogen, USA), and then 1 ug RNA was used to synthesize cDNA using an RT-PCR kit (Clontech, USA). The genes to be analyzed were MAP2, DCX, Tau, NeuroD1, NSE, Nestin and NF-L, and the primers used for the analysis are shown in the following Table 1. The results are shown in FIG. 7.

TABLE 1

Primers for RT-PCR Analysis

| Gene | Direction | Nucleotide Sequence |
|---|---|---|
| MAP2 | Forward (SEQ ID NO: 1) | 5'-CTCAACAGTTCTATCTCTTCTTCA-3' |
| | Reverse (SEQ ID NO: 2) | 5'-TCTTCTTGTTTAAAATCCTAACCT-3' |
| DCX | Forward (SEQ ID NO: 3) | 5'-GGAAGGGGAAAGCTATGTCTG-3' |
| | Reverse (SEQ ID NO: 4) | 5'-TTGCTGCTAGCCAAGGACTG-3' |
| Tau | Forward (SEQ ID NO: 5) | 5'-GTAAAAGCAAAGACGGGACTGG-3' |
| | Reverse (SEQ ID NO: 6) | 5'-ATGATGGATGTTGCCTAATGAG-3' |
| NeuroD1 | Forward (SEQ ID NO: 7) | 5'-CCGACAGAGCCCAGATGTAGTTCTT-3' |
| | Reverse (SEQ ID NO: 8) | 5'-GCCCCAGGGTTATGAGACTATCACT-3' |

TABLE 1-continued

| Primers for RT-PCR Analysis | | |
|---|---|---|
| Gene | Direction | Nucleotide Sequence |
| NSE | Forward (SEQ ID NO: 9) | 5'-GGCGGGCAGTGGAAGAAAA-3' |
| | Reverse (SEQ ID NO: 10) | 5'-AAGTGGAAAGTGCGGAACCC-3' |
| Nestin | Forward (SEQ ID NO: 11) | 5'-CTCTGACCTGTCAGAAGAAT-3' |
| | Reverse (SEQ ID NO: 12) | 5'-GACGCTGACACTTACAGAAT-3' |
| NF-L | Forward (SEQ ID NO: 13) | 5'-GCCAAGAACATGCAGAACGC-3' |
| | Reverse (SEQ ID NO: 14) | 5'-CAGCTTTAATGCGGAACGCC-3' |
| GAPDH | Forward (SEQ ID NO: 15) | 5'-ACCACAGTCCATGCCATCAC-3' |
| | Reverse (SEQ ID NO: 16) | 5'-TTCACCACCCTGTTGCTGTA-3' |

As shown in FIG. 7, the examination of the expression of neuron-related genes (mRNAs) at 5 days after differentiation from the cells treated with lipoic acid revealed that the expression of neuron-related genes increased in all cases treated with 4 mM and 8 mM lipoic acid, compared to the control, and in particular, the expression of neuron-related genes further increased in the case treated with 4 mM lipoic acid.

Experimental Example 3

Western Blot Analysis on Neural Cells

The neural cells cultured in Example 3 were washed with phosphate-buffered saline (PBS) and lysed with radioimmunoprecipitation (RIPA) buffer containing protease inhibitor. The total protein was measured using a BCA® Protein Assay kit (Pierce, USA), and 10 ug protein was electrophoresed on a 10% polyacrylamide gel and transferred to a nitrocellulose membrane. Then, the membrane was blocked with Tris-buffered saline (TBS) containing 5% skim milk and 0.5% Tween® 20 at room temperature for 30 minutes and reacted with antibodies such as anti-NSE, anti-Nestin, Anti-NF-L (Cell Signaling, USA), and β-actin (Sigma, USA) at 4° C. for 16 hours. Subsequently, the membrane was reacted with an anti-mouse or anti-rabbit secondary antibody at room temperature for 1 hour, exposed to ECL™ (Pierce™ Biotechnology, USA), and then imaged using a ChemiDoc™ XRS+Imaging System (BioRad®, USA). The results are shown in FIG. 8.

Figure 8:
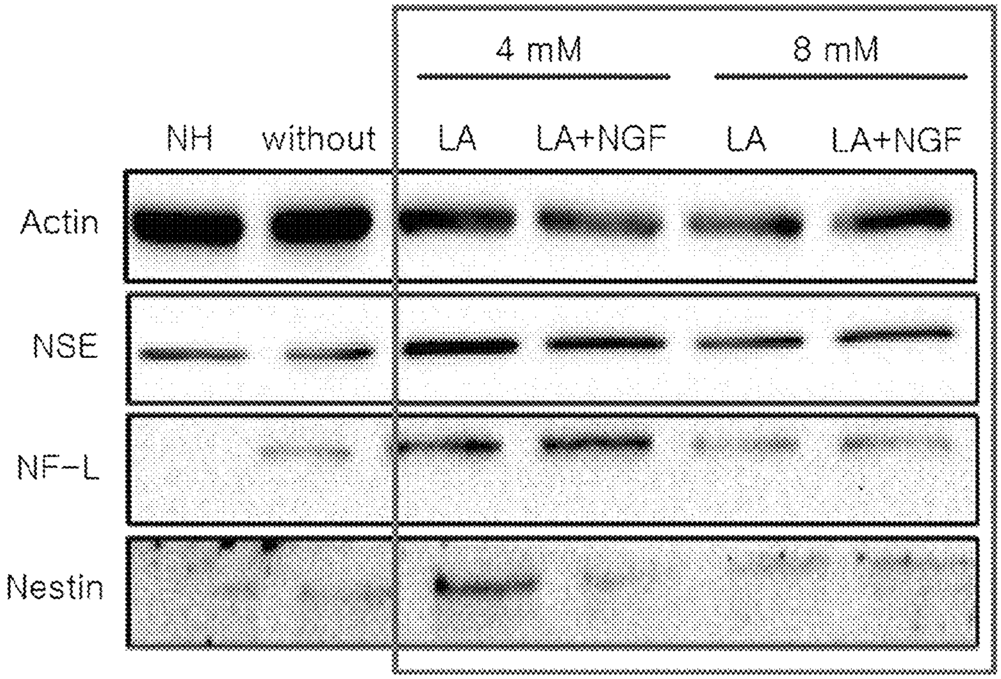
FIG. 8 shows the results of the expression of neuron-specific genes after treating mesenchymal stem cells with lipoic acid according to a chemical neuronal differentiation method, determined by Western blot analysis.

As shown in FIG. 8, the examination of the expression of neuron-associated proteins at 5 days after differentiation from the cells treated with lipoic acid revealed that the expression of neuron-associated proteins increased in all cases treated with 4 mM and 8 mM lipoic acid, compared to the control, and in particular, the expression of neuron-associated proteins further increased in the case treated with 4 mM lipoic acid.

Experimental Example 4

Immunofluorescence (IF) Staining of Neural Cells

The neural cells cultured in Example 3 were fixed on glass coverslips with 4% paraformaldehyde for 10 minutes, blocked with PBS containing 1.5% bovine serum albumin (BSA), and then permeabilized with PBS containing 0.5% Triton™ X-100. Then, the cells were reacted with primary antibodies such as anti-NF-L, anti-MAP2, anti-GFAP, anti-NeuroD1 (Cell Signaling, USA), and anti-tau (Biosource, USA) at 4° C. for 16 hours. Then, the cells were washed with PBS for 10 minutes and reacted with species-specific secondary antibodies such as anti-rabbit IgG-Alexa Fluor® 488 or anti-mouse IgG-Alexa Fluor® 555 conjugate at room temperature for 1 hour. Then, the stained cells were mounted with Vectashield® mounting medium containing DAPI and contrast stained. The cells were examined using a Confocal Laser Scanning Microscope (LSM 510-meta, Germany), and the results are shown in FIG. 9.

Figure 9:
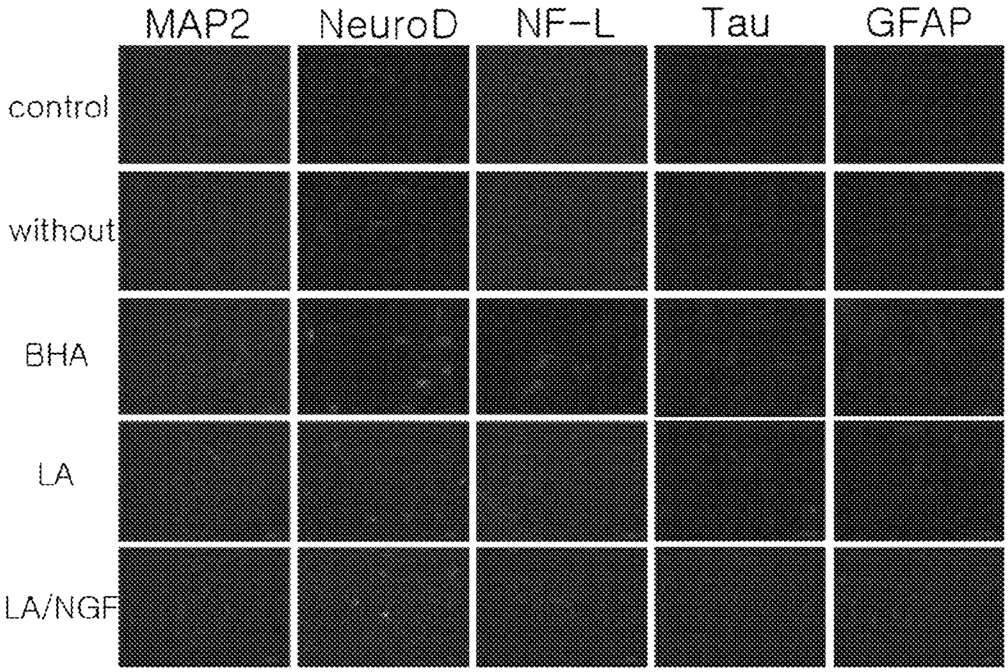
FIG. 9 shows the results of the expression of neuron-specific genes after treating mesenchymal stem cells with lipoic acid according to a chemical neuronal differentiation method, determined by immunofluorescence staining.

As shown in FIG. 9, the examination of the expression of neuron-associated proteins under a microscope at 5 days after differentiation from the cells treated with lipoic acid revealed that the expression of neuron-associated proteins increased in all cases treated with lipoic acid, compared to the control.

The invention claimed is:

1. A method for differentiating a stem cell into a neural cell, the method comprising the steps of:

(a) culturing a stem cell; and (b) treating the stem cell cultured in (a) with a culture medium comprising lipoic acid, albumin, hydrocortisone, and insulin, to differentiate the stem cell into a neural cell, wherein the concentration of the lipoic acid in the culture medium of step (b) is 3 mM to 15 mM; and wherein the concentration of albumin in the culture medium of step (b) is 1 wt % to 5 wt % with respect to the total weight of the medium.

2. The method of claim 1, wherein the stem cell is selected from the group consisting of an embryonic stem cell, an adult stem cell, an induced pluripotent stem cell, a neural stem cell, and a mesenchymal stem cell.

3. The method of claim 1, wherein the stem cell is isolated from at least one selected from the group consisting of human bone marrow, umbilical cord blood, and an adipose tissue.

4. The method of claim 1, wherein the stem cell in step (a) is cultured in at least one medium selected from the group consisting of Dulbecco's modified Eagle's medium (DMEM), DMEM/F-12, F-12, Mc Coy's 5A, RPMI 1640, Williams' medium E, and Iscove's modified Dulbecco's medium (IMDM).

5. The method of claim 1, wherein the hydrocortisone in step (b) is comprised in the culture medium at a concentration of 0.01 μM to 10 μM.

6. The method of claim 1, wherein the insulin in step (b) is comprised in the culture medium at a concentration of 1 mg/ml to 50 mg/ml.

7. The method of claim 1, wherein the culture medium in step (b) further comprises forskolin or a nerve growth factor.

8. The method of claim 7, wherein the nerve growth factor comprises at least one selected from the group consisting of brain-derived neurotrophic factor (BDNF), vascular endothelial growth factor (VEGF), hepatocyte growth factor (HGF), nerve growth factor (NGF), basic fibroblast growth factor (bFGF), glial cell line-derived neurotrophic factor (GDNF), and platelet-derived growth factor (PDGF).

9. The method of claim 7, wherein the forskolin is comprised in the culture medium at a concentration of 0.1 μM to 10 μM.

10. The method of claim 7, wherein the nerve growth factor is comprised in the culture medium at a concentration of 5 ng/ml to 20 ng/ml.

* * * * *